(12) United States Patent
Sun

(10) Patent No.: US 8,785,146 B2
(45) Date of Patent: Jul. 22, 2014

(54) METHOD FOR QUANTITATIVE MEASUREMENTS OF HDL-C AND LDL-C

(75) Inventor: Guojing Sun, Beijing (CN)

(73) Assignee: Beijing Strong Biotechnologies, Inc., Beijing (CN)

( * ) Notice: Subject to any disclaimer, the term of this patent is extended or adjusted under 35 U.S.C. 154(b) by 865 days.

(21) Appl. No.: 12/287,139

(22) Filed: Oct. 6, 2008

(65) Prior Publication Data

US 2009/0246807 A1    Oct. 1, 2009

(30) Foreign Application Priority Data

Apr. 1, 2008    (CN) .......................... 2008 1 0103234

(51) Int. Cl.
*C12Q 1/60*    (2006.01)
(52) U.S. Cl.
USPC ................................................. 435/11; 435/4
(58) Field of Classification Search
USPC .......................................................... 435/11
See application file for complete search history.

(56) References Cited

FOREIGN PATENT DOCUMENTS

| CN | 1379234 A | * | 11/2002 |
|---|---|---|---|
| CN | 1379235 A | * | 11/2002 |

OTHER PUBLICATIONS

Kerscher et al. "Precipitation methods for the determination of LDL-cholesterol", Clinical Biochemistry, 1985, 18:118-125.*
Cobbaert et al. "Performance of a direct, immunoseparation based LDL-cholesterol method compared to Friedewald calculation and a polyvinyl sulphate precipitation method", Eur J Clin Chem Clin Biochem., 1995, 33:417-424.*
Diazyme Laboratories "510(k) Summary" Jan. 3, 2008, p. 16-21.*
Okada et al. "Low-density lipoprotein cholesterol can be chemically measured: a new superior method", J Lab Clin Med., 1998, 132:195-201.*
Arai et al. "Effect of bicarbonate on iron-mediated oxidation of low-density lipoprotein", PNAS, 102(30):10472-10477.*

* cited by examiner

*Primary Examiner* — Bin Shen
(74) *Attorney, Agent, or Firm* — Sofer & Haroun, LLP

(57) ABSTRACT

The present invention relates to a method for direct measurement of high-density lipoprotein cholesterol. (HDL-C) or low-density lipoprotein cholesterol (LDL-C) based on a modified chemical precipitation method, wherein the improvements were made by optimizing the concentrations and proportions of potassium polyvinyl sulfate (PVSK) and polyethylene glycol methyl ether (PEGME) in such a way that the enzymatic reactions are completed before precipitation formations. The method in combination with certain surfactants showed good correlations with other direct methods used for HDL-C or LDL-C determinations.

11 Claims, 2 Drawing Sheets

METHOD FOR QUANTITATIVE MEASUREMENTS OF HDL-C AND LDL-C

RELATED APPLICATION

This application claims the benefit of priority from Chinese Patent Application No. 200810103234.3, filed on Apr. 1, 2008, the entirety of which is incorporated herein by reference.

FIELD OF THE INVENTION

The present invention relates to an improved method for measurements of high-density lipoprotein cholesterol (HDL-C) and low-density lipoprotein cholesterol (LDL-C) and a kit thereof.

BACKGROUND OF THE INVENTION

In blood plasma cholesterol exists and is transported in the form of plasma lipoprotein, that is, nonpolar lipids including cholesterol in blood plasma are combined with hydrophilic lipoprotein, which is water-soluble and thus facilitate their transport. Plasma lipoproteins can be divided into four classes: high-density lipoprotein (HDL), low-density lipoprotein (LDL), very-low-density lipoprotein (VLDL) and chylomicron (CM), wherein the physiological role of LDL is to deliver cholesterol to peripheral tissues, while HDL is to clear the cholesterol in the arterial wall and to deliver it back to the liver. Epidemiological and clinical studies have demonstrated a positive correlation between low-density lipoprotein cholesterol (LDL-C) concentrations and the incidence of arteriosclerotic disease such as coronary heart disease (CHD), while high-density lipoprotein cholesterol (HDL-C) has been demonstrated a negative correlation, that is, it has anti-atherogenic activities. Therefore, LDL-C and HDL-C are the most valuable risk factor index for cardiovascular and cerebrovascular diseases in clinical laboratory measurements of plasma or serum lipids.

Various methods have been used to measure cholesterol in HDL and LDL, including ultracentrifugation, chromatographic and electrophoretic techniques, and precipitation methods. Ultracentrifugation, in which method LDL or HDL are separated according to their density in a ultracentrifuge and then the cholesterol in them is measured, has been the basis for quantitative measurement in most studies and clinical practice; the electrophoretic methods developed later separate lipoproteins on a supported media such as cellulose acetate or agarose gel and then the cholesterol contents are measured by an enzymatic method; in precipitation methods, precipitation reagents coagulate lipoproteins other than HDL, the coagulated lipoproteins are separated by centrifugation and the HDL-C contents are determined by enzymatical measurement of the cholesterol in the supernate; in the first generation of precipitation methods for measurement of LDL-C, Polyvinyl Sulfate (PVS) and polyethylene glycol methyl ether (PEGME) are used to precipitate LDL, the precipitates are collected by centrifugation, and then the cholesterol contents are determined by enzyme reactions. All the methods mentioned above need special instruments, including ultracentrifuge, electrophoresis apparatus and centrifuge etc., and the procedures are complicated, hard to be automated, and thus can not be performed in the clinical laboratory.

SUMMARY OF THE INVENTION

The present invention relates to a method for direct measurement of HDL-C comprising an improved potassium polyvinyl sulfate PVS chemical precipitation method combined with a first surfactant which shows a good reactivity for HDL-C. Cholesterol in lipoproteins other than high-density lipoprotein is encapsulated and insolubilized while not precipitated by improved concentration of PVS and PEGME in combination with other compounds, and the high-density lipoprotein cholesterol is dissolved by a first surfactant which shows a good reactivity for high-density lipoprotein cholesterol and the cholesterol content thereof is determined by an enzyme reaction. The present invention further relates to a method for direct measurement of LDL-C comprising an improved PVS precipitation method, wherein LDL is encapsulated so that it can not be involved in a enzyme reaction, but it is not precipitated, that is no precipitate is formed, and then the cholesterol content in LDL is directly measured under the effect of a combination of a first surfactant and a second surfactant. In details the cholesterol in high-density lipoprotein, very-low-density lipoprotein and chylomicron participates in a Cholesterol esterase reaction under the effect of a first surfactant which shows a good reactivity for lipoprotein cholesterols other than low-density lipoprotein, and the low-density lipoprotein cholesterol is dissolved by a second surfactant and is released for measurement of the content of cholesterol thereof by an enzyme reaction. The resulting hydrogen peroxide of the first step of the enzyme reaction does not need to be removed by the peroxidase, so that sodium azide is not needed to be added in the second step to inhibit the activity of the peroxidase, and a biological preservative can thus be applied. The methods according to the present invention do not need pre-treatment of the sample, i.e. precipitation and centrifugation, and the contents of HDL-C and LDL-C in the sample can be measured directly in a automatic biochemical analyzer.

The improved potassium polyvinyl sulfate PVS chemical precipitation method used herein is an improved concentration and proportion of PVS and PEGME. While measuring the HDL-C, the improved proportion of PVS: PEGME is 1:500-550, and the concentration is 10-20 mg/L and 5 g-11 g/L, respectively; and in order to get a better effect to encapsulate and insolubilize while not precipitate cholesterol in lipoproteins other than high-density lipoprotein, other compounds are added along with PVS and PEGME. Said compounds are those of a good affinity for LDL, VLDL and CM, including polyanion, cyclodextrin sulfate, dextran sulphate, steroid saponins and the like, while the amount used is not subjected to particular limitation and a combination of less coagulation or turbidity is preferred according to the type of the substances and the combination mode; in order to further improve the specificity, divalent metal salts are supplemented simultaneously, which include 0.1 mM-20 mM magnesium salts, calcium salts etc., and magnesium salts are preferred.

While LDL-C is measured directly, improved concentration and proportion of PVS and PEGME are used to encapsulate LDL, and the improved proportion is 1:400-500, and the concentration is 1-20 mg/L and 4 g-10 g/L, respectively; In order to avoid the co-encapsulation of VLDL, a metal chelating agent including EDTA or EGTA etc. which can mask divalent cations is applied with a concentration of 0.1 mM-2 mM; other compounds which have a high affinity for LDL, such as polyanion, heparin sodium, phosphotungstic acid, cyclodextrin sulfate etc. which promote LDL to coagulate, or steroid saponins that have a high affinity for LDL while not result in a precipitate can also be used, whether individually or in combination with one or more within them, while the amount used is not subjected to particular limitation and a combination of less coagulation or turbidity is preferred according to the type of the substances and the combination mode; in order to maintain the biochemical analyzer, it is desirable that magnesium ion is not used or used in a low concentration.

For the selection of a first surfactant, it may be an ionic or a nonionic selective surfactant which shows good reactivity for high-density lipoprotein cholesterol or shows good reactivity for lipoproteins other than low-density lipoprotein, such as polyoxyethylene derivatives or polyoxyethylene-polyoxyethylene condensation compound, including polyoxyethylene higher alcohol ether, polyoxyethylene alkyl ether, polyoxyethylene alkyl phenyl ether, polyoxyethylene alkylene phenyl ether, polyoxyethylene lauryl ether, polyoxyethylene cetyl ether, polyoxyethylene aleyl ether, polyoxyethylene alkylene tribenzyl pheny ether polyoxyethylene alkyl phenyl ether sulfate etc. For the selection of a second surfactant, it may be a surfactant that can react with all the lipoproteins or at least can react with low-density lipoprotein, such as L121, or Triton X100 Tween 20, lipomin LA, Anhitol 24B, Bile acid etc. The above mentioned surfactants which are commercially available include Emulgen series such as Emulgen 108, Emulgen 220, Emulgen 913, Emulgen 709, Emulgen B66, Emulgen A60 (or series A6), Emulgen A90 (or series A9), Emulgen 911, Emulgen L-40 etc. and pluronic series such as pluronic F88, Pluronic F68, Pluronic L121, Pluronic L123, Pluronic L101, Pluronic L108 etc. and Triton x-100 etc. These surfactants can be used individually or in combination, without particular limitations of the amount used. Generally, preferred concentration of the surfactants is 0.01%-3% w/v, and the more preferred concentration is 0.05%-1% w/v.

Cholesterol reaction is performed through cholesterol esterase and cholesterol oxidase, the resulting hydrogen peroxide is treated by peroxidase and then measured through absorbance by 4-amino antipyrine and high sensitive chromogens, and the HDL-C or LDL-C contents are calculated. Commercially available chromogens including N-Ethyl-N-(2-hydroxy-3-sulfopropyl)-3-methylaniline (TOOS), N-(2-Hydroxy-3-sulfopropyl)-3,5-dimethoxyaniline (HDAOS), N-Ethyl-N-(3-methylphenyl)-N'-succinyl ethylenediamine (EMSE) etc. of Dojindo Corporate, Japan. The preferred concentration of the chromogen is 0.1 mM-10 mM.

Besides the above mentioned compounds, surfactants, enzymes and chromogens, reagents used for quantitative measurement of HDL-C or LDL-C, the present methods also include buffer such as Goods buffer, including for example HEPES, MES, MOPS and PIPES etc. The pH of the buffer is 5-10, and pH 6-8 is preferred. The concentration of the buffer is 5-200 mM, with a preferred 20 mM-100 mM.

DETAILED DESCRIPTION OF THE INVENTION

Example 1

Components and Instruction of Kit 1 for Determination of HDL-C

1. Components

There are two components in kit 1 of the present invention for determination of HDL-C, they are:

| First Reagent | |
|---|---|
| MOPS (pH7.0) | 20 mM |
| PVS | 20 mg/L |
| PEGME | 10 g/L |
| α-cyclodextrin sulfate | 2 mM |
| MgSO4 | 5 mM |
| 4AA | 0.5 g/L |
| PC300 | 0.5 g/L |
| Second Reagent | |
| MOPS (pH7.0) | 20 mM |
| Cholesterol esterase | 4 KU/L |
| Cholesterol oxidase | 10 KU/L |
| Peroxidase | 30 KU/L |
| MgSO4 | 5 mM |
| HDAOS | 2 mM |
| Emulgen series A6 | 0.1% w/v |
| PC300 | 0.5 g/L |

2. Instruction for Kit 1

Figure 1:
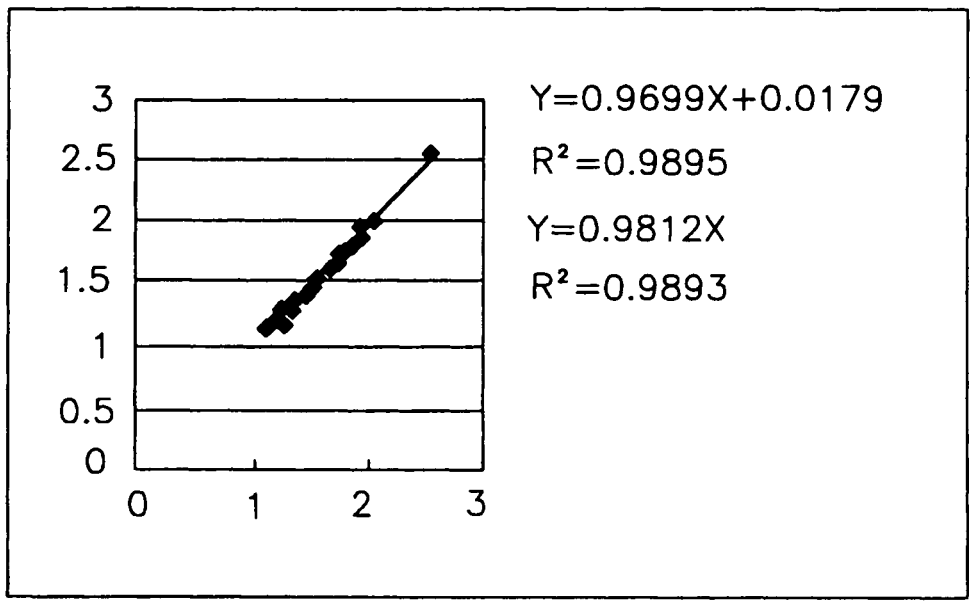
FIG. 1 shows a positive correlation between results obtained with the HDL-C determination kit 1 of the present invention and those obtained with a control reagent.

Olympus AU400 automatic analyzer is used and the procedures are:

The mixture of 3 μl serum and 225 μl First Reagent is incubated at 37° C. for 5 min, and 75 μl Second Reagent is added and reacted for 5 min, and then measured at 600 nm (main) and 700 nm (subsidiary), and the calculation is obtained through the difference of the absorbance. The control experiment is performed using the control reagent according to parameters stated in its instruction. In the methods comparison, the present reagent and the control reagent are calibrated with their respective calibrator serum. Contents of HDL-C in 40 clinical samples are measured simultaneously, and the results are shown in table 1 and FIG. 1, which show an excellent correlation between results obtained with the present method and those obtained with a control reagent.

TABLE 1

| Patients' sera No. | Control Reagent | Reagent of the present invention |
|---|---|---|
| 1 | 2.52 | 2.53 |
| 2 | 1.53 | 1.48 |
| 3 | 1.24 | 1.28 |
| 4 | 1.16 | 1.17 |
| 5 | 1.35 | 1.3 |
| 6 | 1.4 | 1.35 |
| 7 | 1.93 | 1.94 |
| 8 | 1.51 | 1.48 |
| 9 | 1.34 | 1.29 |
| 10 | 1.32 | 1.28 |
| 11 | 1.4 | 1.4 |
| 12 | 1.23 | 1.22 |
| 13 | 1.5 | 1.48 |
| 14 | 1.41 | 1.4 |
| 15 | 1.56 | 1.53 |
| 16 | 1.69 | 1.62 |
| 17 | 1.12 | 1.14 |
| 18 | 1.81 | 1.75 |
| 19 | 1.89 | 1.82 |
| 20 | 1.47 | 1.4 |

TABLE 1-continued

| Patients' sera No. | Control Reagent | Reagent of the present invention |
|---|---|---|
| 21 | 1.27 | 1.19 |
| 22 | 1.66 | 1.62 |
| 23 | 1.32 | 1.29 |
| 24 | 1.49 | 1.46 |
| 25 | 1.3 | 1.33 |
| 26 | 1.3 | 1.27 |
| 27 | 2.03 | 1.99 |
| 28 | 1.41 | 1.38 |
| 29 | 2.04 | 1.99 |
| 30 | 1.39 | 1.36 |
| 31 | 1.31 | 1.31 |
| 32 | 1.75 | 1.67 |
| 33 | 1.75 | 1.73 |
| 34 | 1.78 | 1.75 |
| 35 | 1.17 | 1.18 |
| 36 | 1.41 | 1.41 |
| 37 | 1.34 | 1.35 |
| 38 | 1.73 | 1.66 |
| 39 | 1.92 | 1.86 |
| 40 | 1.21 | 1.18 |

Example 2

Components and Instruction of Kit 2 for Determination of HDL-C

1. Components

There are two components in kit 2 of the present invention for determination of HDL-C, they are:

| First Reagent | |
|---|---|
| HEPES-NaOH (pH7.0) | 20 mM |
| PVS | 20 mg/L |
| PEGME | 10 g/L |
| dextran sulphate | 1 mg/L |
| $MgSO_4$ | 2 mM |
| 4AA | 0.5 g/L |
| PC300 | 0.5 g/L |

| Second Reagent | |
|---|---|
| HEPES-NaOH (pH7.0) | 20 mM |
| Cholesterol esterase | 4 KU/L |
| Cholesterol oxidase | 10 KU/L |
| Peroxidase | 30 KU/L |
| $MgSO_4$ | 5 mM |
| HDAOS | 2 mM |
| Emulgen series A9 | 0.1% w/v |
| PC300 | 0.5 g/L |

2. Instruction for Kit 2

Figure 2:
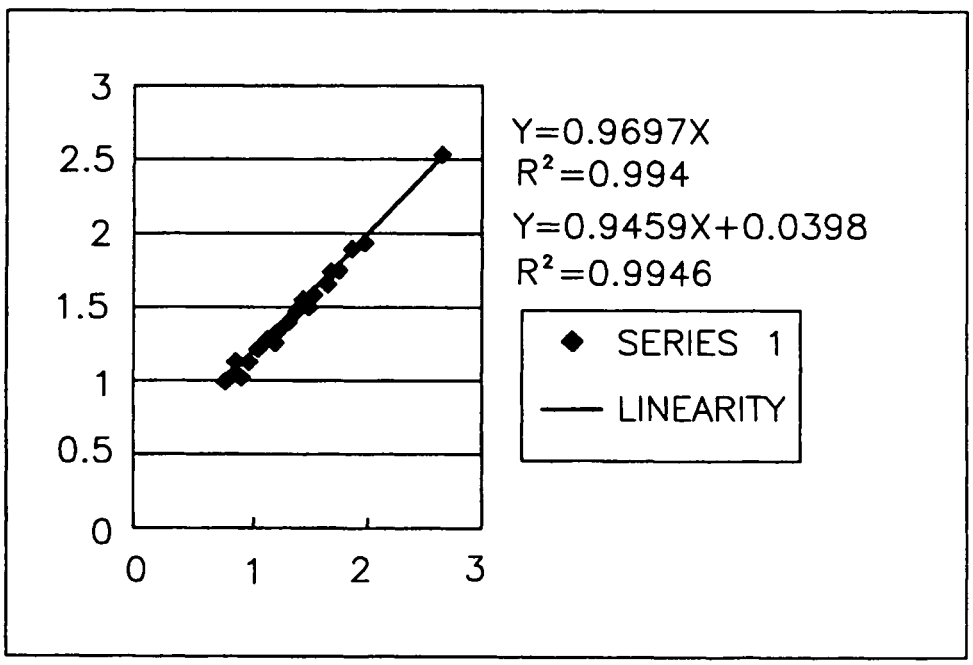
FIG. 2 shows a positive correlation between results obtained with the HDL-C determination kit 2 of the present invention and those obtained with a control reagent.

The procedures and instruments used are the same as described above. Contents of HDL-C in 40 clinical samples are measured simultaneously, and the results are shown in table 2 and FIG. 2, which show an excellent correlation between results obtained with kit 2 of the present method and those obtained with a control reagent.

TABLE 2

| Patients' sera No. | Control Reagent | Reagent of the present invention |
|---|---|---|
| 1 | 1.56 | 1.56 |
| 2 | 1.95 | 1.93 |
| 3 | 1.94 | 1.91 |
| 4 | 1.66 | 1.59 |
| 5 | 1.87 | 1.78 |

TABLE 2-continued

| Patients' sera No. | Control Reagent | Reagent of the present invention |
|---|---|---|
| 6 | 1.02 | 1.04 |
| 7 | 1.8 | 1.77 |
| 8 | 1.29 | 1.29 |
| 9 | 1.8 | 1.75 |
| 10 | 1.81 | 1.76 |
| 11 | 0.98 | 0.97 |
| 12 | 0.98 | 0.98 |
| 13 | 1.23 | 1.21 |
| 14 | 1.08 | 1.09 |
| 15 | 1.62 | 1.58 |
| 16 | 1.64 | 1.6 |
| 17 | 1.77 | 1.75 |
| 18 | 1.79 | 1.76 |
| 19 | 1.36 | 1.33 |
| 20 | 1.35 | 1.32 |
| 21 | 2.06 | 1.96 |
| 22 | 1.83 | 1.77 |
| 23 | 1.74 | 1.68 |
| 24 | 1.35 | 1.28 |
| 25 | 1.84 | 1.77 |
| 26 | 1.08 | 1.02 |
| 27 | 2.68 | 2.58 |
| 28 | 2.05 | 1.96 |
| 29 | 1.82 | 1.78 |
| 30 | 1.17 | 1.12 |
| 31 | 1.46 | 1.4 |
| 32 | 1.77 | 1.67 |
| 33 | 1.6 | 1.55 |
| 34 | 1.14 | 1.1 |
| 35 | 1.32 | 1.28 |
| 36 | 1.61 | 1.54 |
| 37 | 1.78 | 1.69 |
| 38 | 1.82 | 1.75 |
| 39 | 1.66 | 1.58 |
| 40 | 1.51 | 1.48 |

Example 3

Components and Instruction of Kit 1 for Determination of LDL-C

1. Components

There are two components in kit 1 of the present invention for determination of LDL-C, they are:

| First Reagent | |
|---|---|
| MOPS (pH7.0) | 20 mM |
| PVS | 20 mg/L |
| PEGME | 8 g/L |
| EDTA | 2 mM |
| 4AA | 0.5 g/L |
| Cholesterol esterase | 5 KU/L |
| Cholesterol oxidase | 10 KU/L |
| Emulgen series A6 | 0.1% w/v |
| PC300 | 0.5 g/L |

| Second Reagent | |
|---|---|
| MOPS (pH7.0) | 20 mM |
| Peroxidase | 30 KU/L |
| HDAOS | 2 mM |
| Triton X 100 | 1 g/L |
| PC300 | 0.5 g/L |

2. Instruction

Figure 3:
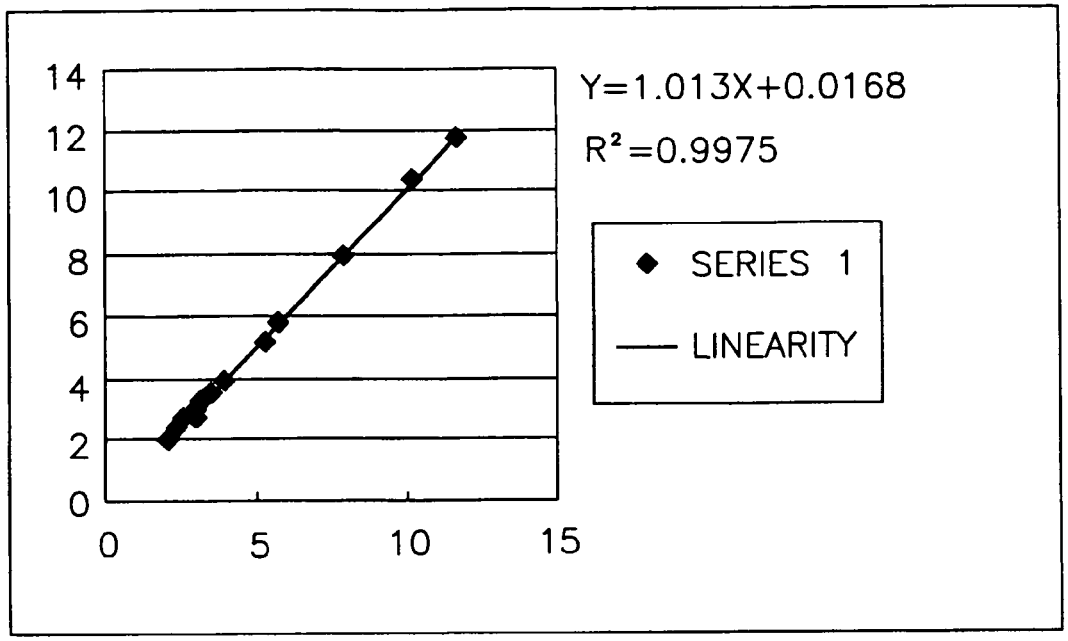
FIG. 3 shows a positive correlation between results obtained with the LDL-C determination kit 1 of the present invention and those obtained with a control reagent.

The procedures and instruments used are the same as described in example 1. Contents of LDL-C in 40 clinical samples are measured simultaneously, and the results are shown in table 3 and FIG. 3, which show an excellent correlation between results obtained with kit 1 for determination of LDL-C of the present invention and those obtained with a control reagent.

TABLE 3

| Patients' sera No. | Control Reagent | Reagent of the present invention |
|---|---|---|
| 1 | 2.57 | 2.51 |
| 2 | 2.76 | 2.74 |
| 3 | 2.6 | 2.57 |
| 4 | 3.37 | 3.35 |
| 5 | 2.58 | 2.6 |
| 6 | 2.27 | 2.32 |
| 7 | 2.78 | 2.73 |
| 8 | 2.96 | 3 |
| 9 | 2.99 | 3.13 |
| 10 | 2.42 | 2.4 |
| 11 | 2.18 | 2.19 |
| 12 | 2.87 | 2.79 |
| 13 | 3.02 | 3.11 |
| 14 | 2.52 | 2.52 |
| 15 | 3.04 | 2.97 |
| 16 | 2.01 | 2.06 |
| 17 | 2.32 | 2.46 |
| 18 | 2.05 | 1.91 |
| 19 | 3.93 | 3.99 |
| 20 | 5.26 | 5.15 |
| 21 | 2.53 | 2.6 |
| 22 | 2.77 | 2.91 |
| 23 | 2.49 | 2.69 |
| 24 | 3.41 | 3.54 |
| 25 | 2.66 | 2.85 |
| 26 | 2.3 | 2.41 |
| 27 | 2.74 | 2.77 |
| 28 | 2.97 | 2.78 |
| 29 | 3.2 | 3.3 |
| 30 | 3.02 | 3.18 |
| 31 | 2.69 | 2.86 |
| 32 | 3.05 | 3.2 |
| 33 | 3.16 | 3.33 |
| 34 | 2.97 | 3 |
| 35 | 2.9 | 2.94 |
| 36 | 11.6 | 11.72 |
| 37 | 10.13 | 10.45 |
| 38 | 7.87 | 7.93 |
| 39 | 5.72 | 5.81 |
| 40 | 3.49 | 3.52 |

Example 4

Components and Instruction of Kit 2 for Determination of LDL-C

Figure 4:
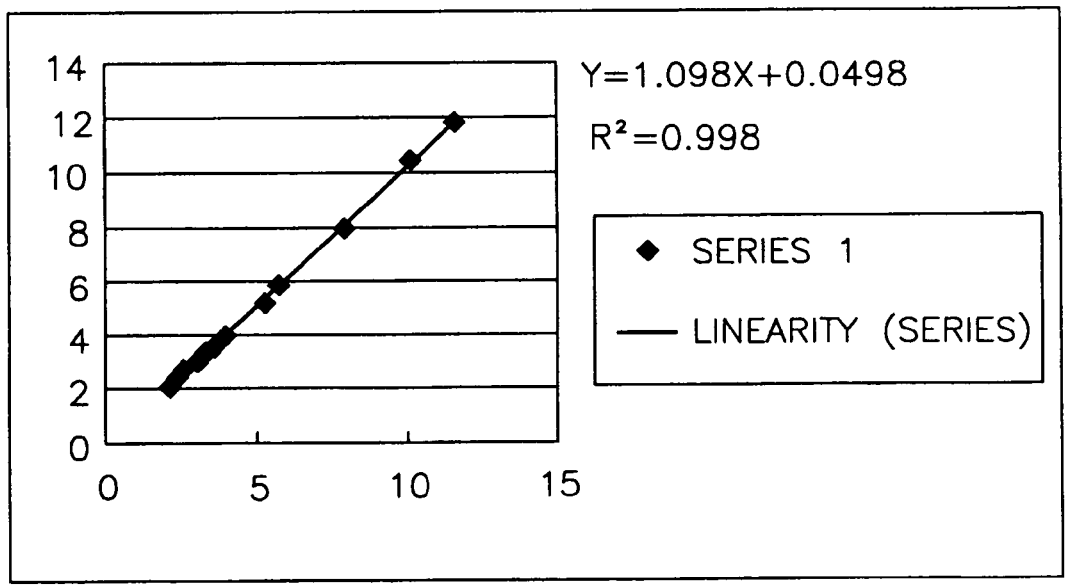
FIG. 4 shows a positive correlation between results obtained with the LDL-C determination kit 2 of the present invention and those obtained with a control reagent.

The contents of LDL-C are measured using the same method as example 3 and compared with control reagents, wherein Emulgen series A6 in First Reagent is substituted by 0.1% w/v Pluronic F88, and Triton X 100 in Second Reagent is substituted by 0.2% w/v Pluronic L121, and the results are shown in table 4 and FIG. 4, which show an excellent correlation between results obtained with the present method and those obtained with a control reagent.

TABLE 4

| Patients' sera No. | Control Reagent | Reagent of the present invention |
|---|---|---|
| 1 | 2.6 | 2.6 |
| 2 | 3.37 | 3.43 |
| 3 | 2.58 | 2.6 |
| 4 | 2.27 | 2.33 |
| 5 | 2.78 | 2.77 |
| 6 | 2.96 | 2.99 |
| 7 | 2.99 | 3.15 |
| 8 | 2.42 | 2.48 |
| 9 | 2.18 | 2.22 |
| 10 | 2.87 | 2.86 |
| 11 | 3.02 | 3.11 |
| 12 | 2.52 | 2.54 |
| 13 | 3.04 | 3.05 |
| 14 | 2.01 | 2.1 |
| 15 | 2.32 | 2.51 |
| 16 | 2.05 | 1.96 |
| 17 | 3.93 | 4.04 |
| 18 | 5.26 | 5.17 |
| 19 | 2.92 | 3 |
| 20 | 2.64 | 2.81 |
| 21 | 2.53 | 2.63 |
| 22 | 2.77 | 2.91 |
| 23 | 2.49 | 2.72 |
| 24 | 3.41 | 3.57 |
| 25 | 2.66 | 2.84 |
| 26 | 2.3 | 2.43 |
| 27 | 2.74 | 2.8 |
| 28 | 2.97 | 2.88 |
| 29 | 3.2 | 3.27 |
| 30 | 3.02 | 3.17 |
| 31 | 2.69 | 2.86 |
| 32 | 3.05 | 3.22 |
| 33 | 3.16 | 3.37 |
| 34 | 2.97 | 3 |
| 35 | 2.9 | 2.92 |
| 36 | 11.6 | 11.72 |
| 37 | 10.13 | 10.45 |
| 38 | 7.87 | 7.93 |
| 39 | 5.72 | 5.81 |
| 40 | 3.49 | 3.52 |

What is claimed is:

1. A method for measuring the contents of high-density lipoprotein cholesterol in a sample, comprising the steps of:
   1) contacting potassium polyvinyl sulfate and polyethylene glycol methyl ether with the sample, said potassium polyvinyl sulfate and polyethylene glycol methyl ether being in an optimized proportion and having optimized concentrations wherein said optimized proportion between potassium polyvinyl sulfate and polyethylene glycol methyl ether is 1:500-550, and said optimized concentrations thereof are 10-20 mg/L and 5 g-11 g/L, respectively for measurement of high-density lipoprotein cholesterol;
   2) measuring the concentrations of high-density lipoprotein cholesterol in the sample enzymatically in combination with at least one surfactant before the formation of precipitation.

2. The method of claim 1, wherein said at least one surfactant is a first surfactant selected from the group consisting of polyoxyethylene higher alcohol ether, polyoxyethylene lauryl ether, polyoxyethylene cetyl ether, polyoxyethylene aleyl ether, polyoxyethylene alkyl ether, polyoxyethylene alkyl phenyl ether, polyoxyethylene alkylene phenyl ether, polyoxyethylene alkylene tribenzyl pheny ether and polyoxyethylene alkyl phenyl ether sulfate.

3. The method of claim 2, further contacting one or more of a compound selected from the group consisting of polyanion, cyclodextrin sulfate, dextran sulphate and steroid saponins.

4. The method of claim 2, further contacting a divalent metal salt having a concentration of 0.1 mM-20 mM.

5. The method of claim 4, wherein said divalent metal is a magnesium salt or calcium salt.

6. A method for measuring the contents of low-density lipoprotein cholesterol in a sample, comprising the steps of:

1) contacting potassium polyvinyl sulfate and polyethylene glycol methyl ether with the sample, said potassium polyvinyl sulfate and polyethylene glycol methyl ether being in an optimized proportion and having optimized concentrations wherein said optimized proportion between potassium polyvinyl sulfate and polyethylene glycol methyl ether is 1:400-500, and said optimized concentrations thereof are 10-20 mg/L and 4 g-10 g/L, respectively, for measurement of low-density lipoprotein cholesterol;
2) measuring the concentrations of low-density lipoprotein cholesterol in the sample enzymatically in combination with at least one surfactant before the formation of precipitation.

7. The method of claim 6, wherein said at least one surfactant is a combination of a first surfactant selected from the group consisting of polyoxyethylene higher alcohol ether, polyoxyethylene lauryl ether, polyoxyethylene cetyl ether, polyoxyethylene aleyl ether, polyoxyethylene alkyl ether, polyoxyethylene alkyl phenyl ether, polyoxyethylene alkylene phenyl ether, polyoxyethylene alkylene tribenzyl phenyl ether and polyoxyethylene alkyl phenyl ether sulfate and a second surfactant including Triton X100, polyoxyethylene-polyoxyethylene condensation compound Pluronic L121, Pluronic L123, Pluronic L101, Pluronic L108, Pluronic F68, Tween 20, lipomin LA, Anhitol 24B, Bile acid.

8. The method of claim 7, further contacting a metal chelating agent having a concentration of 0.1 mM-2 mM to mask divalent cations.

9. The method of claim 8, wherein said metal chelating agent is EDTA or EGTA.

10. The method of claim 7, wherein hydrogen peroxide generated from the first step of enzyme reaction does not need to be removed by peroxidase or catalase, and therefore, sodium azide is not included.

11. The method of claim 7, wherein said second surfactant reacts with lipoproteins or at least with low-density lipoprotein.

* * * * *